(12) United States Patent
Amano et al.

(10) Patent No.: US 8,283,134 B2
(45) Date of Patent: Oct. 9, 2012

(54) CASSETTE FOR FIXING, EMBEDDING AND SLICING BIOLOGICAL TISSUES AND METHOD OF USING THE CASSETTE

(75) Inventors: Shigeru Amano, Kyoto (JP); Yoshinobu Toda, Kyoto (JP)

(73) Assignee: Kyoto University, Kyoto (JP)

( * ) Notice: Subject to any disclaimer, the term of this patent is extended or adjusted under 35 U.S.C. 154(b) by 1128 days.

(21) Appl. No.: 12/086,590

(22) PCT Filed: Dec. 25, 2006

(86) PCT No.: PCT/JP2006/325771
§ 371 (c)(1),
(2), (4) Date: Jun. 16, 2008

(87) PCT Pub. No.: WO2007/074769
PCT Pub. Date: Jul. 5, 2007

(65) Prior Publication Data
US 2010/0167338 A1    Jul. 1, 2010

(30) Foreign Application Priority Data
Dec. 27, 2005  (JP) ................................ 2005-375186

(51) Int. Cl.
*G01N 1/30* (2006.01)
(52) U.S. Cl. ................................................. 435/40.52
(58) Field of Classification Search .................. None
See application file for complete search history.

(56) References Cited

U.S. PATENT DOCUMENTS 5,902,937 A * 5/1999 Amrani et al. .................. 73/856
2004/0175820 A1* 9/2004 Shigematsu et al. ....... 435/287.1

FOREIGN PATENT DOCUMENTS

| JP | 8-211047 | 8/1996 |
| JP | 8-285745 | 11/1996 |
| JP | 9-145571 | 6/1997 |
| JP | 2002-005800 | 1/2002 |

OTHER PUBLICATIONS

International Search Report issued Jan. 23, 2007 in the International (PCT) Application of which the present application is the U.S. National Stage.

* cited by examiner

*Primary Examiner* — Ann Lam
(74) *Attorney, Agent, or Firm* — Wenderoth, Lind & Ponack, L.L.P.

(57) ABSTRACT

A cassette for fixing, embedding and slicing biological tissues includes a base sheet and a lid sheet formed of an elongated plastic sheet which is sliceable and has not less than predetermined strength. The base sheet has grooves as biological tissue receiving portions. The base plate and the lid sheet are formed by folding the plastic sheet along a fold line so that the lid sheet can be selectively opened and closed. Biological tissues are pressed against the bottoms of the grooves with pressing/retaining sponge members secured to the lid sheet at its portions corresponding to the respective grooves. In this state, the biological tissues are fixed by a fixing agent, and the cassette is dehydrated, infiltrated with paraffin as an embedding agent to embed the cassette, thereby forming a block including an embedding frame. The block is then sliced with a microtome to provide good biological tissue specimens.

12 Claims, 13 Drawing Sheets

Fig.1
(a)
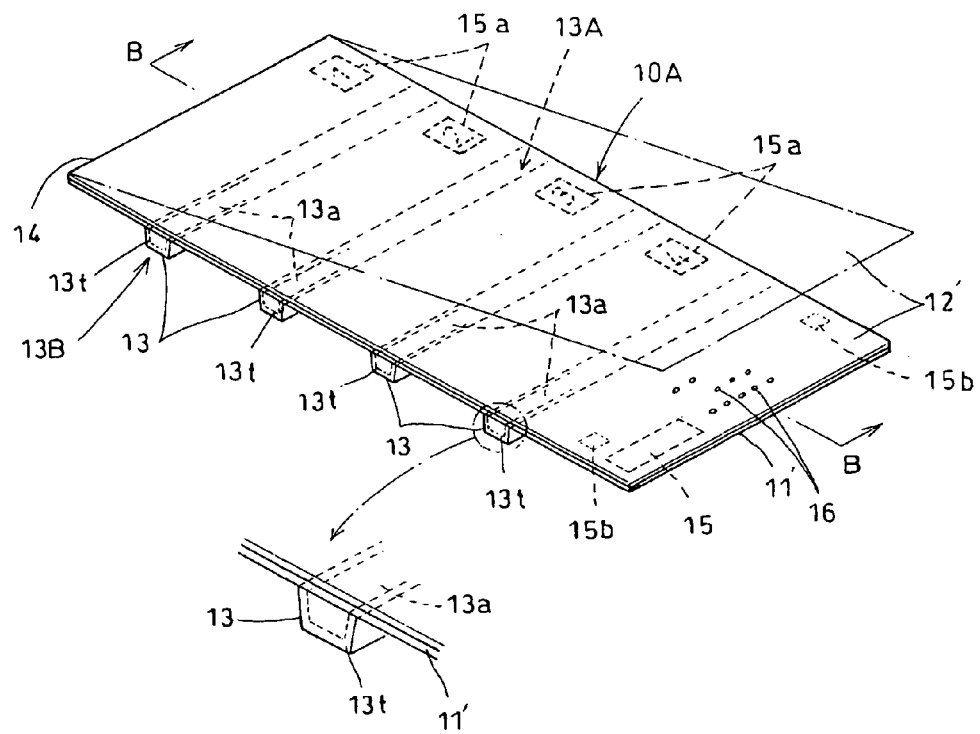
(b)
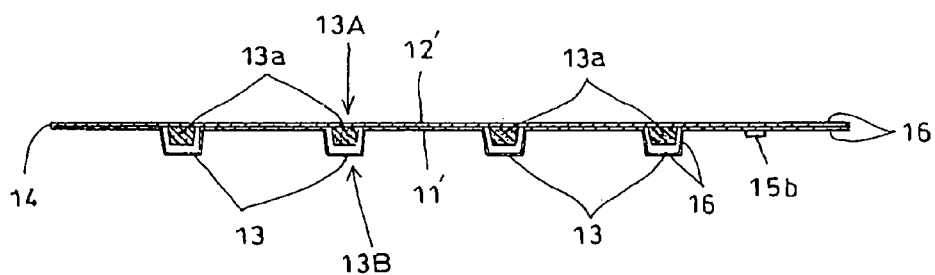

(a)

(b)

Fig.6
(a) 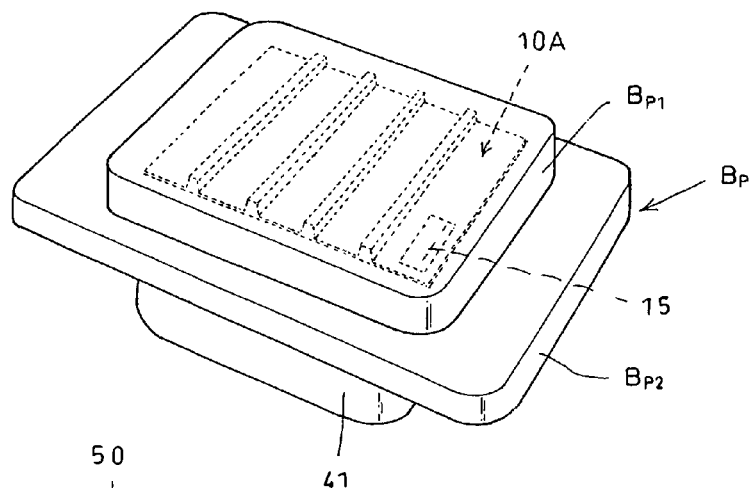
(b) 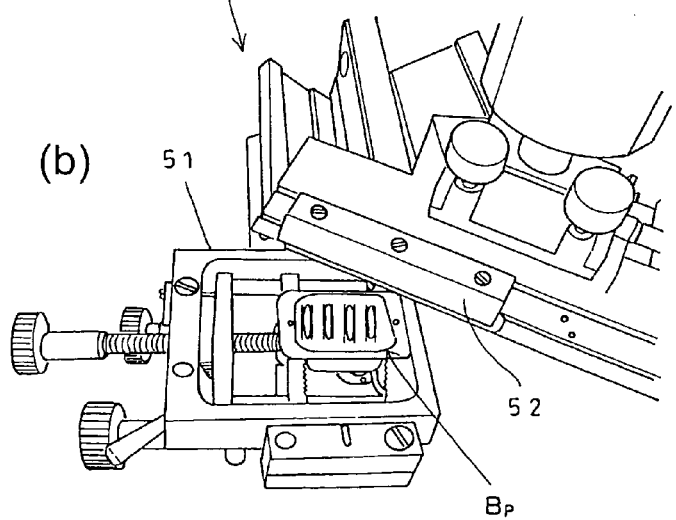

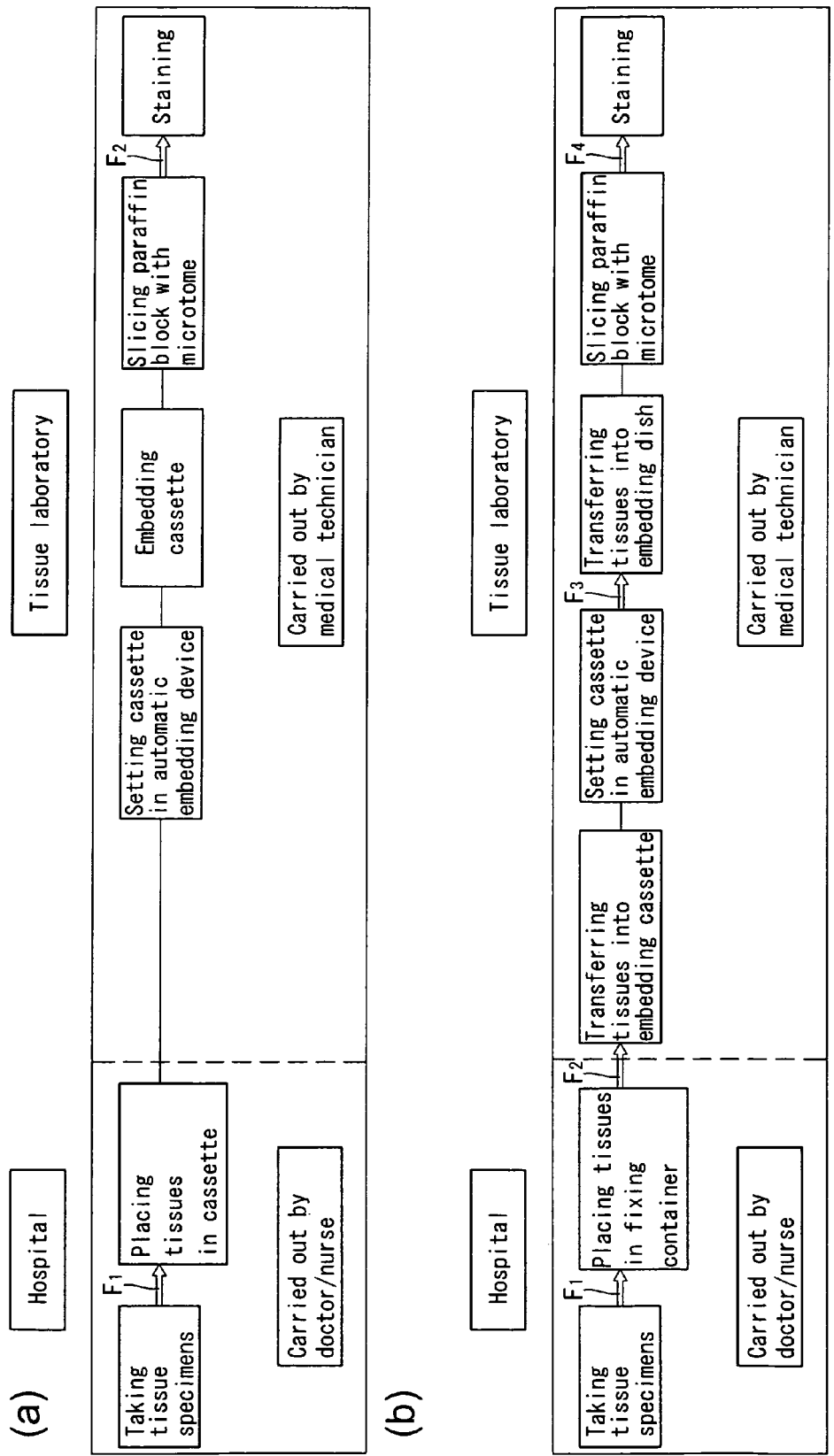

Fig. 13
(a)
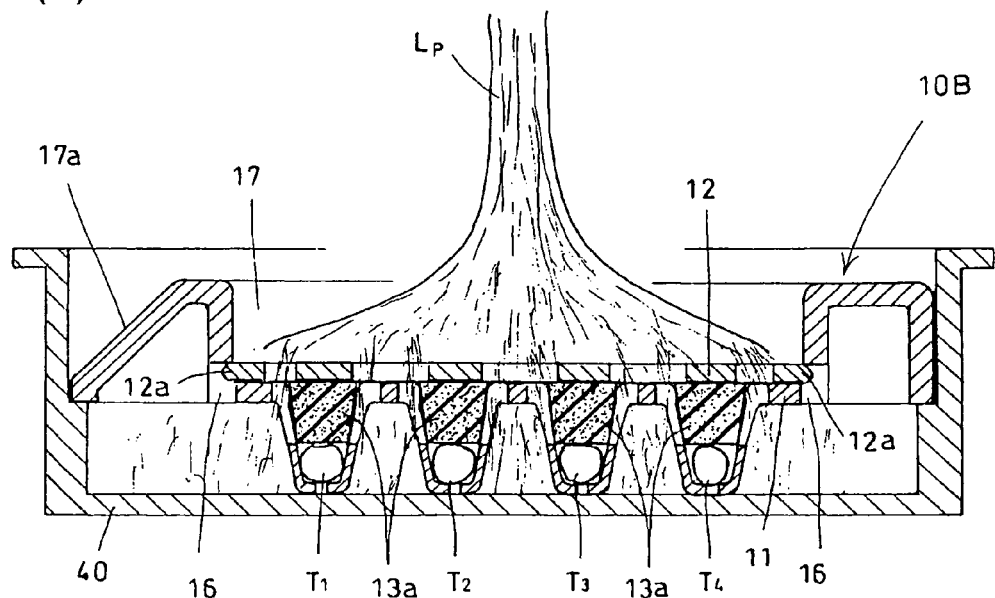
(b)
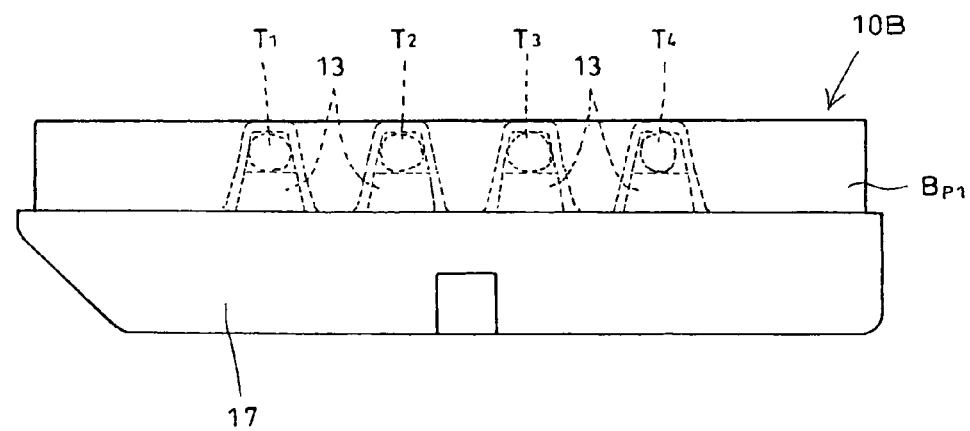

Fig.15

| | Materials | Formalin | Ethanol | Xylol | Chloroform | Paraffin | Heat resistance (65°C) | Slicing properties (3μ) |
|---|---|---|---|---|---|---|---|---|
| Sheet member (0.2~0.3mm) | Hard vinyl chloride | ○ | ○ | ○ | △ | △ | ○ | ○ |
| | Soft vinyl chloride | ○ | ○ | ○ | △ | △ | ○ | ○ |
| | Nylon | ○ | ○ | ○ | ○ | ○ | ○ | ○ |
| | Teflon | ○ | ○ | ○ | ○ | ○ | ○ | ○ |
| | Polypropylene | ○ | ○ | ○ | ○ | ○ | ○ | ○ |
| | Polyether | ○ | ○ | × | × | ○ | ○ | ○ |
| Sponge member | Polyethylene | ○ | ○ | ○ | ○ | × | ○ | △ |
| | Polyurethane | ○ | ○ | ○ | △ | ○ | ○ | ○ |

○ : Usable
△ : Slight problem in use
× : Unusable

| | Tissues embedded in paraffin | Sliced tissues | Microscopic photo of stained tissues (HE staining x200) |
|---|---|---|---|
| Conventional method | | | |
| Method using the cassette according to the invention | | | |

CASSETTE FOR FIXING, EMBEDDING AND SLICING BIOLOGICAL TISSUES AND METHOD OF USING THE CASSETTE

TECHNICAL FIELD

This invention relates to a cassette for fixing, embedding and slicing biological tissues which makes it possible to carry out series of steps including fixation, dehydration, infiltration of an embedding agent, embedding and slicing in such a single cassette, thereby simplifying the forming of tissue specimens while saving labor and eliminating the possibility of mixing of other specimens, and a method of using this cassette.

BACKGROUND ART

For examination of tissues taken from a living organism, for pathological diagnosis of the tissues, and for morphological study in a tissue laboratory, the biological tissues are ordinarily placed in a cassette, fixed, embedded and sliced. More specifically, tissues taken from a living organism are directly put in a bottle containing a fixing agent to fix the tissues. Alternatively, tissues are put in a nylon mesh bag first and then the nylon mesh bag is put in a bottle. Further alternatively, tissues are put in a cassette 1 formed of a porous plate as shown in FIG. 17, its lid (not shown) is closed, and the cassette is put in a bottle containing formalin, pure ethanol or acetone.

In FIG. 17, numeral 2 indicates partitions provided in the container, numeral 3 indicates numerous small holes formed in the bottom of the container, and numeral 4 indicates a slot in which the lid of the cassette is fitted. With biological tissues received, the container is carried to a tissue laboratory. Otherwise, fixed biological tissues are sometimes placed in a new cassette and subjected to the following processes. In the laboratory, for tissues that are placed in a cassette and fixed, the lid of the cassette is opened to check the biological tissues inside and the patient information displayed on the cassette, the lid is closed, and the cassette is set in an automatic embedding device. For smaller biopsy tissues, since they are rarely put in a cassette from the beginning, they are usually transferred from the fixing bottle into a cassette for small tissues at this stage.

For biological tissues that are not put in a cassette but immersed in a fixing solution in a fixing bottle, after the tissues in the fixing bottle have been transferred into a new cassette, the cassette is set in an automatic embedding device. Tissues in a nylon mesh bag can be set in an automatic embedding device as it is. In the automatic embedding device, the tissues in a cassette or in a nylon mesh bag are subjected to dehydration and paraffin infiltration. Upon completion of paraffin infiltration, the cassette or the nylon mesh bag containing the tissues is removed from the automatic embedding device, and transferred into a paraffin tank in an adjacent embedding center. An automatic embedding device automatically carries out series of processes from dehydration to paraffin infiltration.

The embedding center is a device for embedding and cooling tissues infiltrated with an embedding agent. Today, in most laboratories, an automatic embedding device and an embedding center are used. But a cassette containing biological tissues may be manually subjected to dehydration and paraffin infiltration, without using an automatic embedding device. Also, the embedding and cooling steps may be carried out manually without using an embedding center. Then, a separate embedding dish is set on a table in the embedding center, and a small amount of molten paraffin is poured into the embedding dish.

Biological tissues are removed from the cassette or nylon mesh bag taken out of the paraffin tank in the embedding center with tweezers, and set in the embedding dish. An embedding frame is then placed on the embedding dish, molten paraffin is poured into the dish from above, and the embedding dish including the embedding frame, which has now become integral with the biological tissues, is placed on a cooling station adjacent to the embedding center to cool it. When the paraffin solidifies, the block comprising the now integral biological tissues and embedding frame is removed from the embedding dish. The block is set in a microtome and sliced. This conventional fixing, embedding and slicing method is described in Patent document 1, too.

Patent document 1: JP Patent Publication 8-211047A

SUMMARY OF THE INVENTION

Object of the Invention

In such a conventional fixing, embedding and slicing method, if biopsy tissues are taken from a living organism and put in a fixing bottle or a cassette immediately thereafter, due to the presence of free space around the tissues, the tissues tend to be deformed when they solidify. This may pose problems when forming specimens. Also, because biological tissues have to be removed from a cassette or a nylon mesh bag with tweezers in a laboratory, and transferred into a separate embedding dish for embedding, biological tissues may be partially crushed and damaged, thus making it difficult to form good specimens. If a plurality of biological tissues in a cassette are erroneously placed in a different sequence in an embedding dish, biological tissues may be contaminated with each other. This could influence the examination results, thus leading to grave misdiagnosis. This problem is pointed out in Patent document 1, too.

But in the method of Patent document 1, a plurality of biopsy specimens are simply placed on the bottom surface of a cassette, and are not placed in grooves so that linear tissues can be fixed in the original linear state, or in recesses so that irregularly shaped tissues can be fixed in the original irregular shapes. Thus, if e.g. strips of tissues taken from human liver, kidney or prostate, or small irregularly shaped tissues taken from e.g. gastric mucosa or colon mucosa are simply placed in an embedding cassette, it is sometimes difficult to press the entire tissues against the bottom of the embedding dish in an orderly manner. This may make it difficult to obtain examination information over the entire length of the biopsy specimens when the tissues are sliced with a microtome.

In the method of Patent document 1, biopsy specimens are solidified using a fixing agent containing glucomannan and formalin, the embedding cassette is placed in a capsule container, its outer periphery is gelled and solidified with a gelling agent containing methanol and formalin, and the capsule container is carried to a pathological laboratory. In the pathological laboratory, the embedding cassette is taken out of the capsule container, placed in a separate container, and dehydrated with a dehydrating agent. Then after degreasing and penetration of an embedding agent, the embedding cassette is taken out of the container, biopsy specimens are taken out of the embedding cassette in the form of a gel block and placed in an embedding dish, the empty embedding cassette is placed thereon, an embedding agent such as paraffin is poured from above, and the block is solidified by cooling to obtain an embedding block.

This method requires a gelling agent and other treating agents, and also requires various instruments and complicated processing steps because biological tissues have to be transferred into a plate, a capsule, another container, and an embedding dish. Thus, this method is scarcely used in actual medical field. In FIG. 9(b), which is shown in comparison with FIG. 9(a), which shows the processing steps according to the present invention (which will be described in detail later), the "processing steps" according to this conventional method are shown. The thick arrows f (f1 to f4) in FIG. 9(b) indicate steps carried out manually by a doctor, nurse or medical technician using tweezers. During these steps, tissues may be deformed or crushed, or misplaced.

A first object of the present invention is to provide a cassette for fixing, embedding and slicing biological tissues which is made of a sliceable material, which makes it possible to place biological tissues in this cassette, and fix, embed and slice the tissues in this same cassette, thereby simplifying the processing steps and saving labor, and also eliminating the possibility of deformation and crushing of the tissues, and the possibility of misplacement of the tissues, and which makes it possible to embed the tissues while being pressed against the bottom of the cassette, whereby good and accurate diagnostic results of pathological tissues are obtainable.

Another object of the invention is to provide a method of fixing, embedding and slicing biological tissues in which biological tissues are fixed, embedded and sliced in a single cassette for fixing, embedding and slicing biological tissues obtained by the first object, whereby the possibility of misplacement of biological tissues can be eliminated, and biopsy tissues are obtainable while preventing deformation, crushing and misplacement.

Means to Achieve the Object

In order to achieve the first object, the present invention provides a cassette for fixing, embedding and slicing biological tissues, the cassette comprising a base plate formed of a sliceable blank plate which has hardness and strength both higher than predetermined levels and on which biological tissues can be placed, a lid plate formed by bending the blank plate forming the base plate, or formed of a separate blank plate and detachably coupled to the base plate, the base plate having a tissue receiving portion for receiving biological tissues, and a pressing/retaining member detachably coupled to the lid plate or provided separately from the lid plate for immovably pressing and retaining the biological tissues, the base plate and the lid plate being formed with numerous small holes.

In order to achieve the second object, the present invention provides a method of fixing, embedding and slicing the abovementioned cassette, comprising the steps of placing biological tissues in the tissue receiving portion of the base plate, closing the lid plate, immersing the cassette in a fixing agent, fixing the biological tissues with the pressing/retaining member, setting the cassette in an automatic embedding device, dehydrating the cassette, placing the cassette in an embedding agent infiltration tank to infiltrate an embedding agent into the biological tissues in the cassette, removing the cassette from the automatic embedding device, placing the cassette in an embedding dish, pouring an embedding agent into the embedding dish from over the cassette, thereby embedding the cassette in the embedding agent, removing the cassette from the embedding dish to form a block containing the cassette, setting the block on a microtome for forming tissue slices, and slicing the block.

From another aspect of the invention, there is provided a method of fixing, embedding and slicing the abovementioned cassette, comprising the steps of placing biological tissues in the cassette, pouring, immediately thereafter, an embedding agent for forming frozen pieces into the cassette, closing the lid plate 12, freezing the cassette, and slicing the cassette with a cryostat. The cryostat is a device including a freezing room kept at about minus 15 to minus 30 degrees Celsius and in which a microtome is mounted for slicing frozen biological tissues.

Now description is made on how the cassette for fixing, embedding and slicing biological tissues according to the invention is used. With the lid plate opened, biological tissue are placed in tissue receiving portions of the base plate, the biological tissues are pressed against the bottoms of the tissue receiving portions with the pressing/retaining members to keep the biological tissues immovable on the bottoms of the tissue retaining portions, thereby retaining the shapes of the tissues when they are placed in the cassette. In this state, the lid plate is closed, and the cassette is placed in a container containing formalin and carried to a tissue laboratory. In the tissue laboratory, the cassette is taken out of the container, set in an automatic embedding device and dehydrated, an embedding agent comprising paraffin is infiltrated into the cassette, the cassette is then removed from the automatic embedding device and placed in an embedding dish with the biological tissues retained therein, and an embedding agent is poured into the dish from over the cassette to embed the cassette. If an embedding frame is necessary, it is placed on the cassette before pouring an embedding agent. As used in this invention, the terms "base plate" and "lid plate" also refer to a base sheet and lid sheet, respectively. Below, relatively thin base plate and lid plate are referred to as a base sheet and a lid sheet, respectively, and relatively thick ones are referred to as a base plate and a lid plate, respectively.

The cassette is then cooled and removed from the embedding dish to form a block containing the cassette in which biological tissues are retained. By slicing the block with a microtome, good biological tissue specimens are obtained. Slicing as used herein refers to slicing biological tissues using a special blade called a microtome. Fixing as used herein refers to coagulating or denaturing protein of the tissues with a chemical selected according to the type of staining, such as formalin, a mixture of picric acid, formalin and acetic acid, pure ethanol or acetone, thereby changing the liquid-state biological tissues into solid-state tissues, and thus preventing rotting of the tissues and keeping the tissue structure. (An aqueous solution of formalin is ordinarily used for this purpose.)

Dehydration refers to removing water in the tissues by replacing the water content in the biological tissues with ethanol, an ethanol-methanol mixture or acetone. Ordinarily, ethanol is used for this purpose. Infiltration of an embedding agent refers to immersing the dehydrated biological tissues in an embedding agent such as paraffin or celloidin, which is melted by means of an intermediate agent to allow the embedding agent to infiltrate into the biological tissues. Paraffin is ordinarily used for this purpose.

Because the cassette is made of a material that can be sliced with a microtome, once biological tissues are placed in this cassette, the later steps can be carried out without the need to transfer the tissues to another container. This simplifies the processing steps, saves labor, reduces the possibility of crushing of the tissues, and prevents misplacement of tissues. Also, since the tissues are pressed against the bottom of the cassette, it is possible to minimize deformation of the tissues taken while they are fixed and embedded. Thus, it is possible to obtain good slices of tissues. Embedding refers to solidifying the biological tissues by infiltrating paraffin, Paraplast, celloidin or epoxy resin (one of them is selected according to the type of specimens to be formed). Ordinarily, paraffin is used for this purpose.

Advantages of the Invention

As described above, because the cassette for fixing, embedding and slicing biological tissues according to the present invention comprises a base plate on which biological tissues can be placed, a lid plate which can be opened and closed relative to the base plate, the base plate having a tissue receiving portion for receiving biological tissues, and a pressing/retaining member detachably coupled to the lid plate or provided separately from the lid plate for immovably pressing and retaining the biological tissues, the base plate and the lid plate being formed with numerous small holes, it is possible to form slices of biological tissues by placing biological tissues in the cassette, fixing the biological tissues with a fixing agent together with the cassette, while preventing their movement, dehydrating them, infiltrating an embedding agent, embedding the cassette in an embedding agent to form a block, mounting the block on a microtome, and slicing the block, which contains the cassette.

Further, because the method of fixing, embedding and slicing the abovementioned cassette according to the present invention comprises the steps of placing biological tissues in the tissue receiving portion of the base plate, closing the lid plate, immersing the cassette in a fixing agent, fixing the biological tissues with the pressing/retaining member, embedding the cassette in an embedding agent, removing the cassette from the embedding dish to form a block, mounting the block on a microtome, and slicing the block, which contains the cassette, the biological tissues can be processed without handling them with e.g. tweezers after they are taken and placed in the cassette until they are sliced and stained, so that good sliced specimens of biological tissues can be formed easily while preventing misplacing and mistaking of tissues. Thus, it is possible to save time and labor. The cassette can therefore be advantageously used in the field of morphological examination of tissues including clinical examination.

BRIEF DESCRIPTION OF THE DRAWINGS

FIG. 1(a) is an external perspective view of a cassette for fixing, embedding and slicing biological tissues according to a first embodiment; and FIG. 1(b) is a sectional view taken along line B-B of FIG. 1(a).

FIG. 6(a) is an external perspective view of a block formed on the embedding dish with the embedding dish removed; and FIG. 6(b) shows how the block is set in a microtome for slicing the block.

FIG. 9(a) is a flowchart of processing steps of biopsy tissues according to the present invention, and FIG. 9b is a similar flowchart for a prior art arrangement.

FIG. 13(a) is a sectional view showing how paraffin is poured into this cassette; and FIG. 13(b) is a sectional view showing how the cassette is set in a microtome and sliced.

FIG. 15 is a table showing the results to chemical resistance, heat resistance and slicing property tests for sheet materials and sponge materials.

Figure 2:
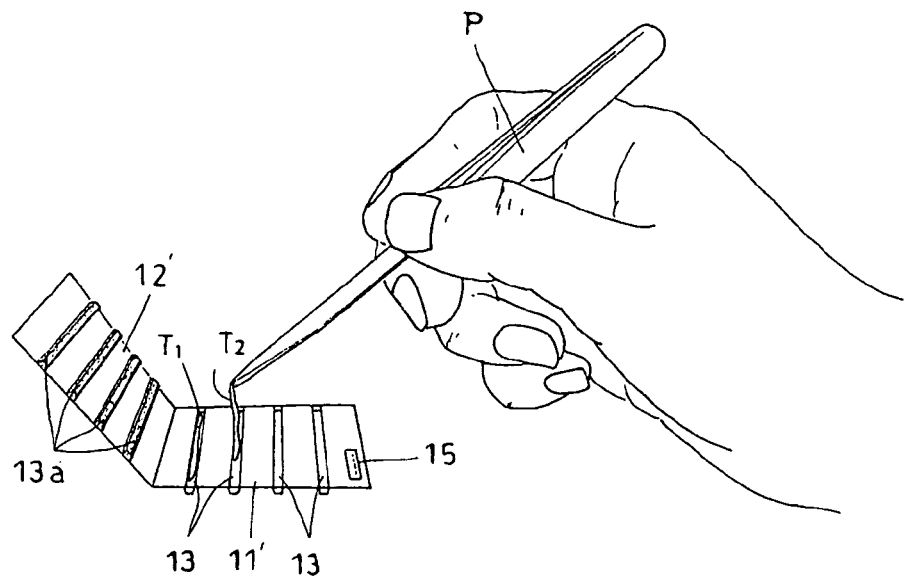
FIG. 2 shows how biological tissues are placed in the cassette of FIG. 1(a).

DESCRIPTION OF NUMERALS 10A, 10A', 10A", 10A'", 10AR. Cassette for fixing, embedding and slicing biological tissues
10B, 10B', 10B", 10B'". Cassette for fixing, embedding and slicing biological tissues
11. Base plate
11'. Base sheet
12. Lid plate
12'. Lid sheet
12a. Protrusion
13A. Pressing/retaining member
13a. Sponge member
13B. Tissue receiving portion
13. Groove
13b. Recess
13b'. Partition plate
13c. Frame
14. Fold line
15. Patient information display portion
15b. Fitting portion
16, 16a. Hole
16b. Engaging hole
17. Edge plate
17a. Support member
18. Grip
20. Fixing bottle
21. Cap of fixing bottle
30. Paraffin infiltration tank (in an automatic embedding device)
31. Container
40. Embedding dish
41. Embedding frame
50. Microtome

DETAILED DESCRIPTION OF THE INVENTION

Figure 8A:
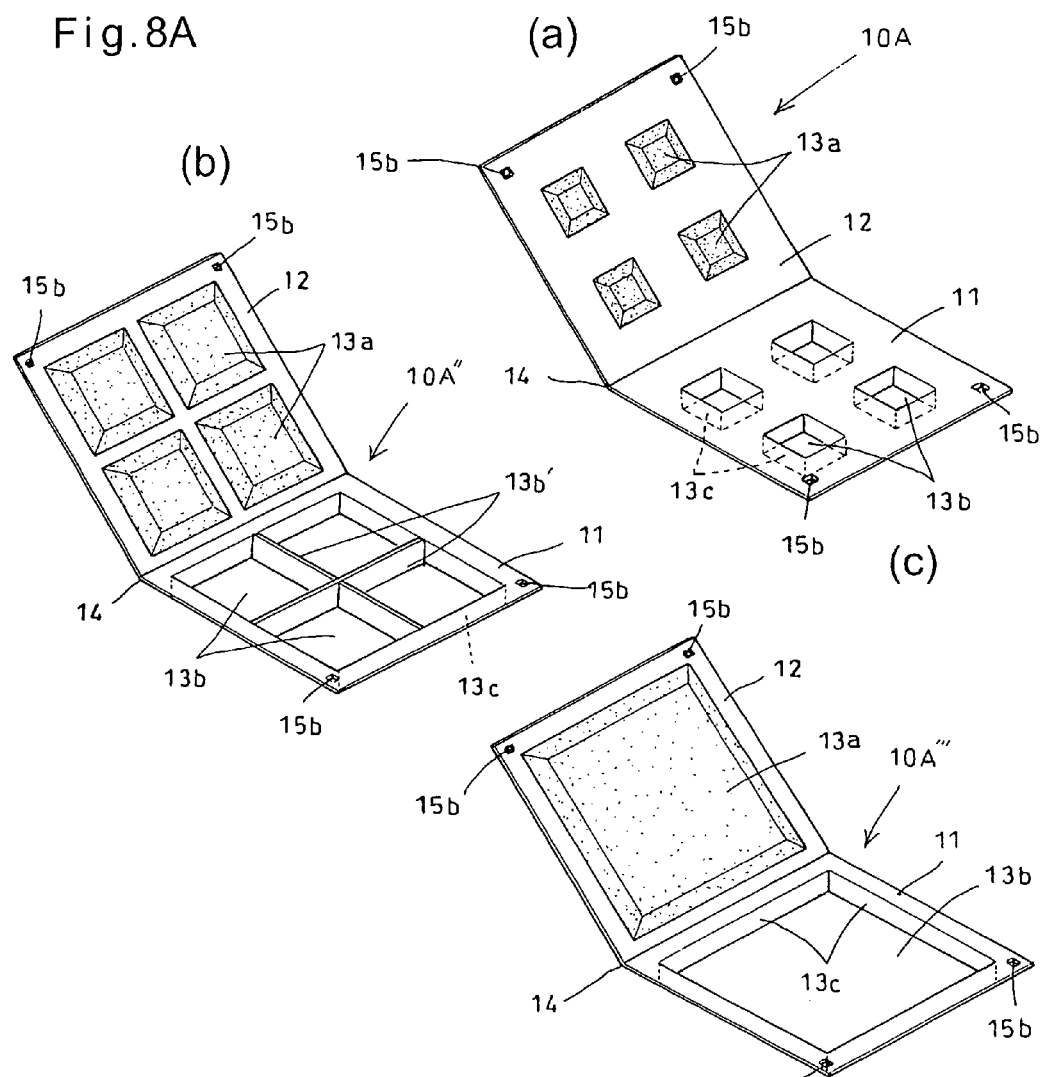
FIGS. 8A(a) to 8A(c) are external perspective views of cassettes for retaining biological tissues according to first to third modified examples.

Now the embodiments are described with reference to the drawings. FIGS. 1(a) and 1(b) show a cassette 10A of the first embodiment for fixing, embedding and slicing biological tissues. In particular, FIG. 1(a) is a perspective view of the cassette, and FIG. 1(b) is a sectional view taken along line B-B of FIG. 1(a). The cassette 10A has a plurality of grooves in its bottom, and is used to fix, embed and slice strips of biopsy tissues of e.g. liver, prostate or kidney. FIG. 8A shows a cassette according to another embodiment of the invention, which will be described hereinafter. As shown, the cassette 10A comprises a single elongated thin plastic sheet that is folded in half along a fold line 14 to form a lower base sheet 11' and an opposed upper lid sheet 12'. The plurality of grooves 13 are formed in the base sheet 11' in rows.

Sponge members 13a are stuck on the bottom surface of the lid sheet 12' at positions corresponding to the respective grooves 13 of the base sheet 11'. The sponge members 13a serve as pressing/retaining members 13A for pressing biological tissues against the bottoms of the grooves 13 and retaining them in position. For this purpose, the sponge members have elasticity sufficient to press the tissues against the bottoms of the grooves 13 but not so hard as to crush them. The sponge members can be sliced too. But the sponge members 13a may not necessarily be stuck on the lid sheet. They may be simply received in the respective grooves 13. With this arrangement, tissues are placed in the grooves 13 after removing the sponge members 13a from the grooves 13, the sponge members are then set in the grooves 13 again to cover the tissues, and the lid sheet 12' is closed. As the pressing/retaining members 13A, instead of the sponge members 13a, an adhesive or any other member having an equivalent function may be used to adhere and retain biological tissues.

The base sheet 11' and the lid sheet 12' are made of a material that is water-resistant, resistant to fixing agents such as formalin, alcohol and acetone, resistant to organic solvents such as xylene and chloroform, is not deteriorated by paraffin, is not markedly deformed or modified when the temperature changes within the range of −30 to 65° C., and allows the grooves 13 of the cassette as tissue receiving portions 13B which contain biological tissues to be sliced to thicknesses of several micrometers with a microtome. At a corner of the base sheet 11', a patient information display portion 15 is provided where patient information such as the patient's name or code is shown. Beside each groove 13 of the base sheet 11', a groove number display portion 15a is provided for distinguishing sample tissues from each other.

In the embodiment shown, the base sheet and the grooves are made of two polypropylenes having different hardnesses and thicknesses and selected from synthetic high-molecular weight compounds (plastics). In particular, while both polypropylenes are hard ones, the base sheet 11' is harder and the grooves 13 are softer. The cassette 10A shown is 20 mm in length and 34 mm in width. Its grooves are 3 mm wide and 2 mm deep, its base sheet 11' and lid sheet 12' are 0.4 to 1 mm thick, and its grooves 13 are 0.1 to 0.2 mm thick (wall thickness of the entire U-shaped grooves). The sponge members 13a have dimensions corresponding to the grooves of the base sheet, i.e. 2.5 mm wide, 1.5 mm high and 20 mm long. But the sizes and thicknesses of the sheets and the sponge members are not limited to these values.

While not shown, small holes having a diameter of about 0.5 to 1.0 mm are formed in the bottom and sides of each groove 13 of the base sheet 11', end plates 13t closing the ends of the grooves 13, and the portions of the lid sheet 12' corresponding to the grooves 13, at the rate of 10 to 40/100 mm$^2$, to allow infiltration of liquid into the cassette during fixing, dehydration, infiltration of embedding agent, and embedding. The end plates 13t have the same hardness and thickness as the grooves 13. In the embodiment shown, the sheets and the grooves are made of polypropylenes, but they may be made of other materials, provided such materials are sufficiently resistant to the abovementioned various chemicals and temperature changes and can be sliced. Such other materials include Teflon (registered trademark), polystyrene, nylon, ABS resin, specially treated paper and other biological material.

Near the free ends of the sheets, a plurality of (two in the embodiment shown) fitting portions 15b each comprising a protrusion formed on one of the sheets and a recess formed in the other for receiving the protrusion are formed. With this arrangement, when the lid sheet 12' is superposed on the base sheet 11' with biological tissues held therebetween, the protrusions are fitted in the respective recesses, thereby joining the sheets together. The protrusions of the fitting portions 15b can be disengaged from the respective recesses by pulling one of the sheets away from the other sheet. Instead of such fitting portions, other means may be used to detachably join the lid sheet 12' to the base sheet 11' e.g. by joining the peripheral edges of the sheets together with clips or staples or through an adhesive.

The cassette 10a is a cassette container used mainly for clinical examination of biological tissues. It is used to prepare reliable and favorable stained tissue specimens by placing elongated strips of tissues of e.g. prostate taken during human biopsy in this cassette, and carrying out, in the same cassette, necessary steps including fixing, dehydration, infiltration of embedding agents, embedding and slicing. These steps can be carried out in a simple manner with minimum labor. Referring to FIGS. 1 to 9, description is made of these steps carried out in the cassette 10A.

First, as shown in FIGS. 1(a) and 1(b), as a preparatory step, the patient information including the name of the target patient, date of biopsy, part of the body where tissues are taken is entered in the patient information display portion 15. Then, as shown in FIG. 2, with the lid sheet 12' opened relative to the base sheet 11', a doctor or a nurse picks up biological tissues T1, T2 . . . with tweezers P and sets them in the respective grooves 13 of the base sheet 11' in a predetermined order. Then, the lid sheet 12', on which the sponge members for pressing and retaining the tissues are stuck, is closed, i.e. superposed on the base sheet 11' to press the biological tissues against the bottoms of the respective grooves. The sponge members may be merely received in the grooves, instead of sticking them on the lid sheet. Immediately thereafter, the cassette, which now contains the biological tissues, is put in a fixing bottle containing fixing solution.

Figure 3:
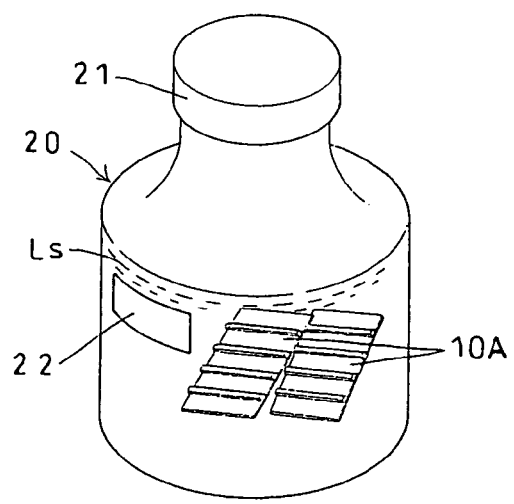
FIG. 3 is a perspective view of the cassette of FIG. 1(a), which is put in a fixing container.
Figure 4:
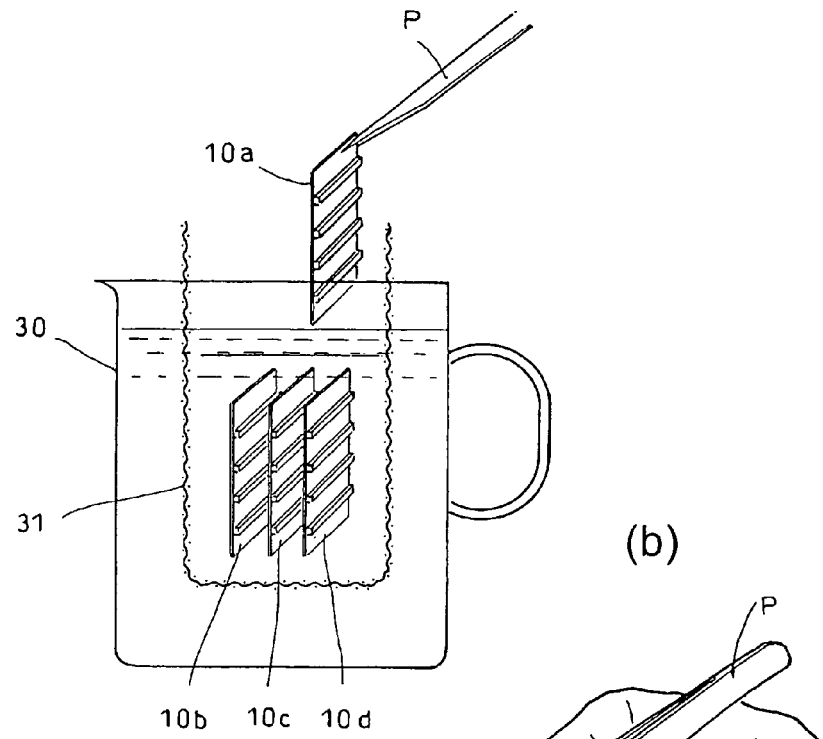
FIG. 4(a) shows how the cassette of FIG. 1(a) is taken out of a container in a paraffin infiltration tank of an automatic embedding device.
FIG. 4(b) shows how the cassette is placed on an embedding dish.

The fixing bottle 20, which is used to transport a plurality of such cassette 10A, contains a fixing solution Ls in such an amount that the cassettes 10A are completely immersed in the solution as shown in FIG. 3. The cassettes are immersed in the fixing solution Ls. The cap 21 of the fixing bottle 20 as a cassette container is then closed, and the hospital name or the like is entered in a display portion 22 of the fixing bottle 20. The steps so far described are carried out in a hospital or a clinic where the patent belongs. The bottle is then transported from the hospital to a tissue laboratory. At the hospital where there is the tissue laboratory, the bottle is transported from a tissue biopsy room to a tissue laboratory.

Once in the tissue laboratory, the cap 21 of the fixing bottle 20 is opened, and the cassettes 10A are taken out and set in an automatic embedding device, in which the cassettes 10A is dehydrated and then moved into a paraffin infiltration tank. Upon completion of paraffin infiltration, as shown in FIG.

4(a), the plurality of cassettes 10A (10a to 10d) are taken out of a container 31 (made of wire netting) of the paraffin infiltration tank 30 with tweezers, and moved into a paraffin tank set on an embedding center. On the embedding center, as shown in FIG. 4(b), each cassette is placed in an embedding dish 40 which contains a small amount of paraffin with its bottom down.

Figure 5:
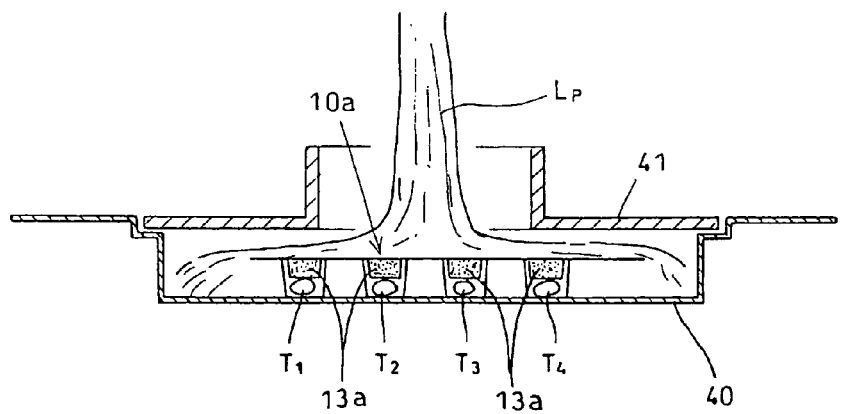
FIG. 5 is a sectional view showing how molten paraffin is poured into the embedding dish from above with the cassette of FIG. 1(a) placed in the embedding dish and a embedding frame placed thereon.
Figure 7:
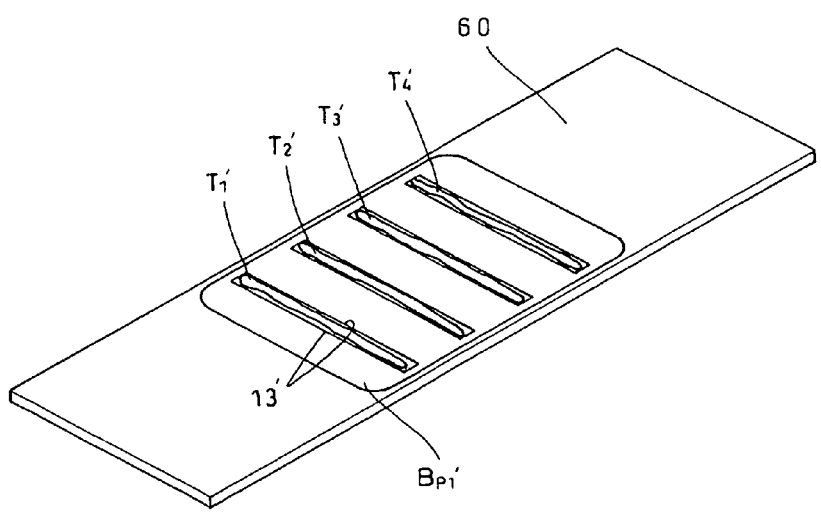
FIG. 7 shows how slices of biological tissues are stuck on a glass slide.

Then, on the embedding center, as shown in FIG. 5, an embedding frame 41 is set in the embedding dish 40 from above the cassette. In this state, a molten embedding agent Lp such as paraffin is poured from a melt tank into the embedding dish 40. By filling up the embedding dish with the embedding agent Lp to the limit, not only is the cassette 10A completely immersed in the embedding agent Lp, but any space between the embedding frame 41 and the recess of the embedding dish 40 is filled with the embedding agent Lp. Then, from above the embedding frame 41, the cassette is pressed down toward the embedding dish with tweezers P. In this state, the embedding dish 40 is moved onto a cooling table (not shown) provided next to the embedding center and allowed to cool down for a predetermined time period until the embedding agent Lp in the embedding dish 40 and the embedding frame 41 solidifies.

The embedding dish 40 is removed from the block comprising the thus solidified embedding agent Lp. The thus obtained block Bp to be sliced, which contains the cassette 10A, is shown in FIG. 6(a) (with the embedding frame 41 arranged downward). The cassette is embedded in the paraffin block with its bottom pressed against the paraffin surface. The block Bp comprises an upper block layer Bp1 containing the cassette 10A, and a lower block layer Bp2 containing the embedding frame 41. The patient information on the patient information display portion 15 can be seen thorough the paraffin of the paraffin block Bp.

As shown in FIG. 6(b), the block Bp is set on a block retaining portion 51 of the microtome 50, and is cut a plurality of times from its top end surface by a cutting blade 52 into a plurality of extremely thin slices Bp1' on the order of micrometers according to the depth of cut. By cutting the block Bp containing biological tissues with the microtome, it was possible to obtain as good slices as those obtained by conventional methods. The slices Bp1' were placed on a glass slide shown in FIG. 7. Then staining procedures were carried out. The slices Bp1' comprises slices T1 to T4 of the biological tissues, and slices 13' of the material forming the cassette. When the slices Bp1' are stained by a usual staining method, only the biological tissues are stained with the slices 13' of the material forming the cassette not stained. Thus, it was possible to stain the slices favorably in the same manner as with conventional methods.

In the first embodiment, the base sheet 11' and the lid sheet 12' are formed by folding a single elongated sheet. But these sheets may comprise separate sheets having fitting portions which allow the sheets to be detachably joined to each other. In the embodiment, in order to receive biological tissues, the grooves 13 are formed in the bottom surface of the base sheet. Also, the grooves 13 of the embodiment are in the form of a plurality of strips extending parallel to each other. But instead, L-shaped or U-shaped grooves of any other shape may be formed. Also, biological tissues may be retained not in grooves but, as will be described later, on a flat surface, in recesses or in spaces defined by partition plates, or by any other retaining structure.

In FIGS. 9(a) and 9(b), these "steps" are compared. FIG. 9(a) shows the steps carried out using the cassette embodying the invention. FIG. 9(b) shows the steps carried out using a conventional cassette. As will be apparent from these figures, in the conventional arrangement, tissue specimens taken in a hospital have to be transferred first into an embedding cassette and then into a tray of an embedding device in a tissue laboratory. By using the cassette embodying the present invention, once the tissues are placed in the cassette (F1), it is never necessary to transfer the tissue to another container until the final staining step (F2) is complete. This is true for the following modified embodiments and the second embodiment, too.

FIG. 8A shows (first to third) modified examples (cassettes 10A', 10A" and 10A''') of the first embodiment. The cassette 10A' of the first modified example shown in (a) of FIG. 8A includes a base sheet 11' having frames 13c protruding downwardly (in a direction away from the lid sheet 12') from the base sheet 11' and defining recesses 13b as tissue receiving portions having a predetermined depth for receiving biological tissues. This cassette is used to retain a plurality of small, irregularly shaped biopsy tissues, such as biopsy tissues of gastric mucosa, colon mucosa and uterine cervical mucosa. Like the grooves 13, the frames 13c defining the recesses 13b and the bottoms of the recesses 13b are made of a sliceable material thinner than the base sheet 11'.

The cassette 10A" of the second modified example shown in (b) of FIG. 8A includes a base sheet 11' formed with a plurality of recesses 13b as tissue receiving portions having a predetermined depth and defined by a frame 13 protruding downwardly from the base sheet 11' and partition plates 13b' for receiving biological tissues. This cassette is used to retain middle-sized tissues such as tissues of removed colon polyp or tissues obtained by transurethral resection of bladder tumor. In this example, too, like the grooves 13, the frame 13c and the partition plates 13b' defining the recesses 13b and the bottoms of the recesses 13b are made of a sliceable material thinner than the base sheet 11'. The partition plates 13b' may be arranged in any shape other than a cross. If the total space of the recesses 13b is increased from the state shown to the limit, the width of the base sheet 11' decreases to a value equal to the thickness of the frame 13c. In this case, the top portion of the frame 13c is considered to constitute the base sheet 11'.

The cassette 10A''' of the third modified example shown in (c) of FIG. 8A includes a base sheet 11' formed with a recess 13b as a tissue receiving portion having a predetermined depth and defined by a frame 13c protruding downwardly from the base sheet 11' and a flat bottom for receiving biological tissues. This cassette is used to retain large-sized flat tissues such as liver operation materials or stomach operation materials. In this example, too, like the grooves 13, the frame 13c defining the recess 13b and the bottom of the recess 13b are made of a sliceable material thinner than the base sheet 11'.

To the lid sheet 12' of any of the first to third modified examples, sponge members 13a for pressing and retaining tissues, similar to those used in the first embodiment, are stuck. The sponge members 13a are shaped corresponding to the recess or recesses defined in the base sheets 11' of the respective modified examples. In this example, too, if the space of the recess 13b is increased from the state shown to the limit, the width of the base sheet 11' decreases to a value equal to the thickness of the frame 13c. In this case, the top portion of the frame 13c is considered to constitute the base sheet 11'.

The sponge members 13a may be merely received in the grooves 13b, instead of sticking them on the lid sheet 12'. In this case, the sponge members are taken out of the recesses 13b, tissues are placed in the recesses, the sponge members are placed in the recesses to cover the tissues, and the lid sheet 12' is closed. While not shown, small holes having a diameter of about 0.5 to 1.0 mm are formed in the bottom, sides and ends of the recesses formed in the base sheet 11' and in the portions of the lid sheet 12' corresponding to the recesses of the base sheet 11', at the rate of 10 to 40/100 mm$^2$, to allow infiltration of liquid into the cassette during fixing, dehydration, infiltration of embedding agent, and embedding. In any of the first to third modified examples, the base sheet 11' and the lid sheet 12' are joined together in the same manner as in the first embodiment.

Using the cassette having recesses in the base sheet 11' for retaining a plurality of small, irregularly shaped biopsy tissues, such as biopsy tissues of gastric mucosa, colon mucosa and uterine cervical mucosa, the cassette having recesses defined by partition plates for retaining middle-sized tissues such as tissues of removed colon polyp or tissues obtained by transurethral resection of bladder tumor, or the cassette having a flat-bottomed recess in the base sheet 11' for retaining large-sized flat tissues such as liver operation materials or stomach operation materials, series of steps including fixation, dehydration, embedding and slicing are carried out basically in the same manner as the steps carried out using the cassette of the first embodiment, which has grooves.

Figure 8B:
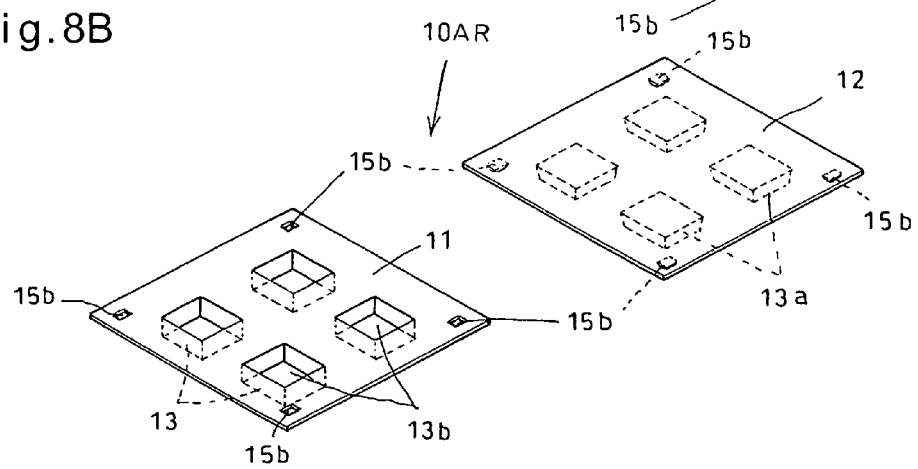
FIG. 8B is an external perspective view of a detachable type of cassette according to a further modified example of the first modified example.

In any of the first to third modified examples, the base sheet 11' and the lid sheet 12' are folded along the fold line 14. But instead, as shown in FIG. 8B, a base sheet 11' and a lid sheet 12' which are separate members from each other may be detachably joined together. The cassette 10AR shown in 8B corresponds to the first modified example. The cassettes comprising separate base and lid sheets and corresponding to the second and third modified examples are not shown.

In this case, because the sheets are not folded along the fold line 14, it is necessary to form along the edges of the sheets a plurality of fitting portions 15b each comprising a protrusion formed on one of the sheets and a recess formed in the other of the sheets for receiving the protrusion. In order to retain biological tissues between the base sheet 11' and the lid sheet 12', the protrusions are engaged in the respective recesses, thereby joining the sheets together. The cassette can be opened by pulling one sheet away from the other until the protrusions disengage from the respective recesses.

The base sheet 11' and the lid sheet 12' may be detachably joined together along their edges by means other than the fitting portions 15b, such as by clips or staples. In the arrangement in which the base sheet 11' and the lid sheet 12' are formed by folding a single sheet material, the sheets are ordinarily made of the same material and have the same thickness (though they may be made of different materials and have different thicknesses). In the arrangement in which the separate base and lid sheets are detachably joined together, because it is not necessary to slice the lid sheet 12' with the microtome in the final step, the lid sheet 12' may be made of a different (harder and stronger) material and have a different (larger) thickness than the base sheet 11'.

Figure 10:
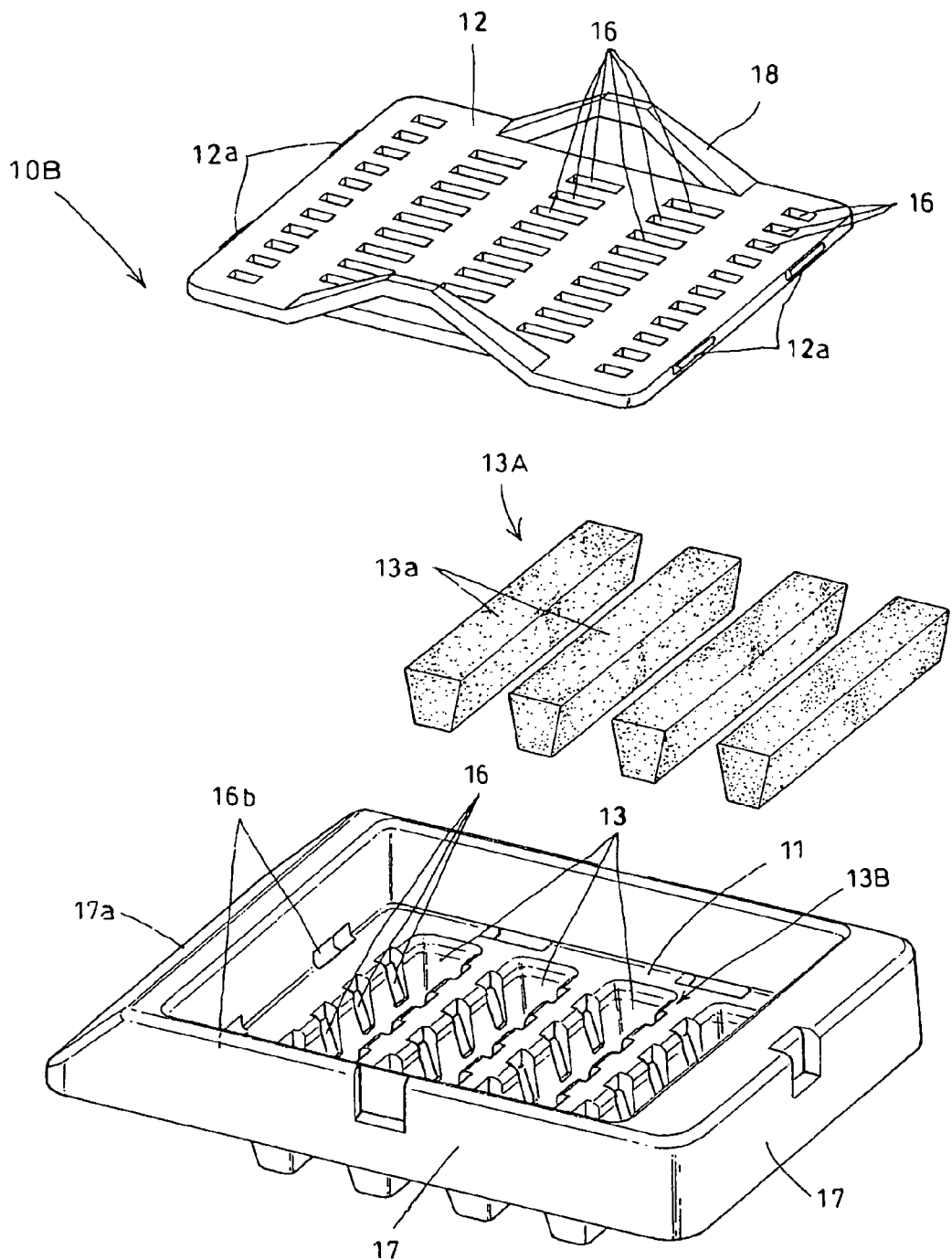
FIG. 10 is an exploded perspective view of a cassette for fixing, embedding and slicing biological tissues according to a second embodiment.

FIG. 10 shows an exploded perspective view of a cassette 10B according to a second embodiment of the present invention. The cassette 10B includes a base plate 11 corresponding to the base sheet 11' of the cassette 10A of the first embodiment, and an edge plate (side plate) 17 made of the same material as the base plate 11 and surrounding the base plate 11. The edge plate has a support member 17a. The cassette 10A further includes a lid plate 12 which is separate from the base plate 11 and different in shape and structure from the base sheet 11', and separate pressing and retaining members 13A which are not stuck on the back of the lid plate 12. The lid plate 12 has grips 18. The grips 18 may be provided at locations other than shown.

Elements of this embodiment that are identical or similar to those of the first embodiment are denoted by identical or similar numerals (for example, the base plate and the lid plate, which correspond to the base sheet 11' and the lid sheet 12' of the first embodiment, are denoted by numerals 11 and 12, respectively), and their description is omitted. Below, what differs from the first embodiment is mainly described. The base plate 11 and the lid plate 12 have larger wall thicknesses than the base sheet 11' and the lid sheet 12' of the cassette 10A of the first embodiment, respectively, and have three-dimensional structures. Thus, the word "plate" is used. But as used herein, the terms "base plate" and "lid plate" are to be understood to encompass the terms "base sheet" and "lid sheet", respectively.

As shown in FIG. 10, the edge plate 17 is a box-shaped member surrounding the base plate 11. The lid plate 12 is detachably fitted in the edge plate 17 with no gap therebetween. Protrusions 12a for engagement may be formed on portions of the lid plate 12 other than shown. After placing pieces of biological tissues each in one groove 13 with tweezers, the pressing and retaining pieces 13A, which are in the form of sponge members 13a that are not stuck on the lid plate 12, are set in the respective grooves 13 to cover the tissues. But instead, as in the first embodiment, the sponge members 13a may be stuck on the back of the lid plate 12 at its portions corresponding to the respective grooves.

Like the grooves 13 of the first embodiment, the grooves 13 are formed in the flat portion of the base plate 11 in its range slightly narrower than its entire width. Description of their detailed structure is omitted. Corresponding to the respective engaging protrusions 12a formed on the lid plate 12, engaging holes 16b are formed in the base plate 11 near the ends of its short sides. But if protrusions 12 are formed at portions other than shown, the engaging holes 16a are also provided at other portions corresponding to the protrusions 12a. The support member 17a is provided on one side of the edge plate 17. The support member 17a serves to reinforce the cassette 10B, and also makes it easier to hand-carry the cassette from e.g. a hospital to a tissue laboratory. The size of the support member 17a and/or the base plate 11 may be changed. On the slope of the support member, such information as the patient number is displayed.

In the embodiment, the base plate, the members forming the grooves, the edge plate and the lid plate are made of polypropylenes selected from synthetic high-molecular weight compounds (plastics). The base plate 11 and the members forming the grooves 13, the edge plate 17, and the support member 17a have different thicknesses from each other. They are all made of hard polypropylenes. But the base plate 11, the edge plate 17 and the support member 17a are made of a harder polypropylene than the members forming the grooves 13. The cassette 10B shown is 27 mm in length and 40 mm in width. Its grooves are 2 mm wide and 4 mm deep, its base plate 11 and lid plate 12 are 1.0 to 1.5 mm thick, and its grooves 13 are 0.1 to 0.2 mm thick (wall thickness of the entire U-shaped grooves). The sponge members 13a have dimensions corresponding to the grooves of the base sheet, i.e. 2 mm wide, 2 mm high and 24 mm long.

Figure 11:
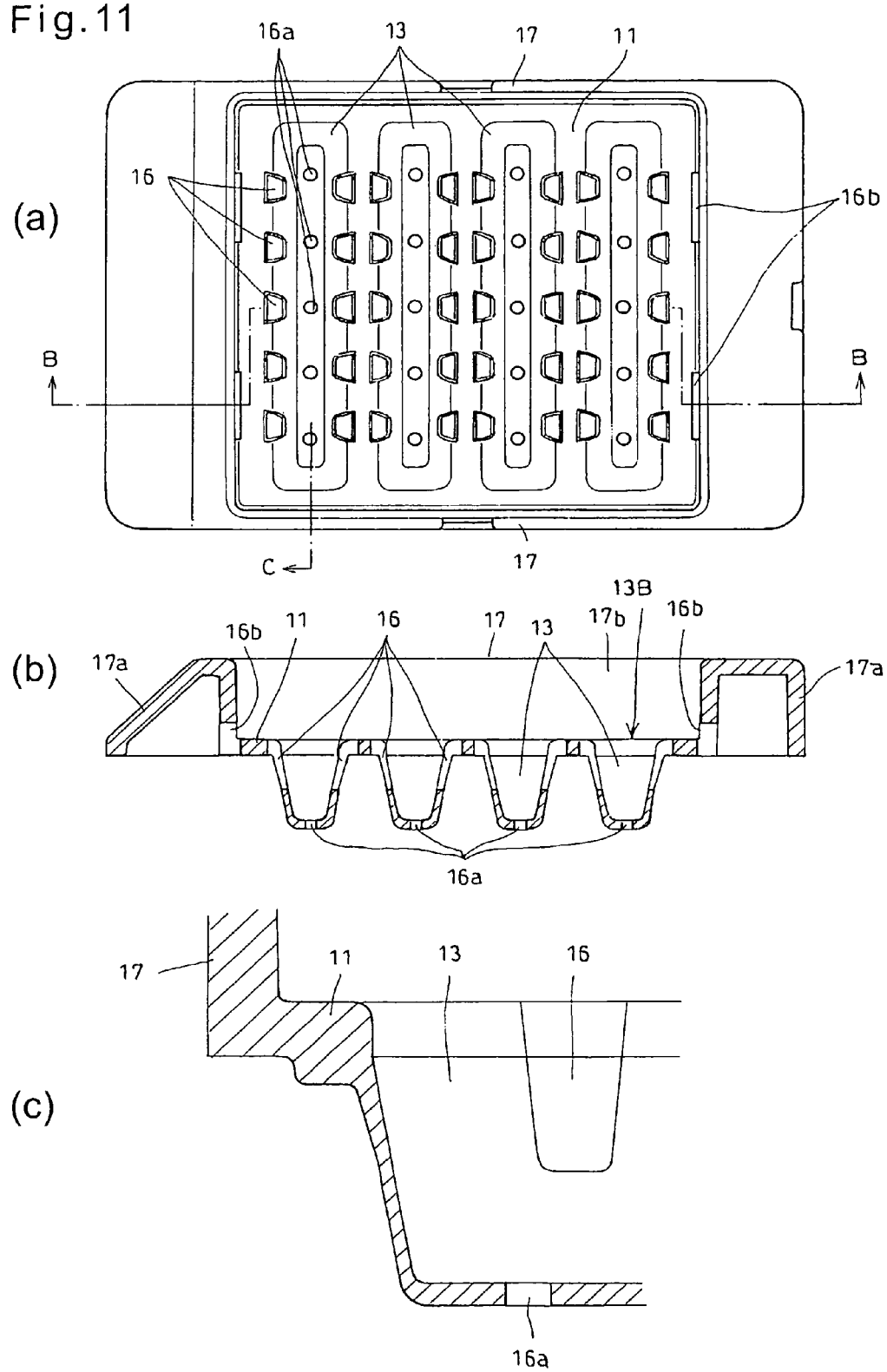
FIG. 11(a) is a plan view of the cassette of FIG. 10.
FIG. 11(b) is a sectional view taken along line B-B of FIG. 11(a)
FIG. 11(c) is a sectional view taken along the arrow C of FIG. 11(a).

As shown in FIG. 11, numerous holes 16a having a diameter of about 0.5 to 1.0 mm, or similar small holes are formed in the bottoms, sides and end walls of the grooves 13 of the base plate 11 and in the lid plate 12 at its corresponding portions to allow infiltration of liquid into the cassette during fixing, dehydration, infiltration of embedding agent, and embedding. (In the example shown, holes 16a are formed in the bottoms of the grooves 13, the small holes 16 comprise elongated holes formed in the side walls of the grooves 13, and the engaging holes 16a are cutouts each corresponding to one of protrusions 12a of the lid plate 12.) In the embodiment shown, the base plate, lid plate, edge plate, and the members forming the grooves may be made of materials other than polypropylene, provided such materials are sufficiently resistant to the abovementioned various chemicals and temperature changes and can be sliced. Such other materials include polyurethane, Teflon (registered trademark), polystyrene, vinylon, nylon, ABS resin, specially treated paper and other biological material.

Figure 12:
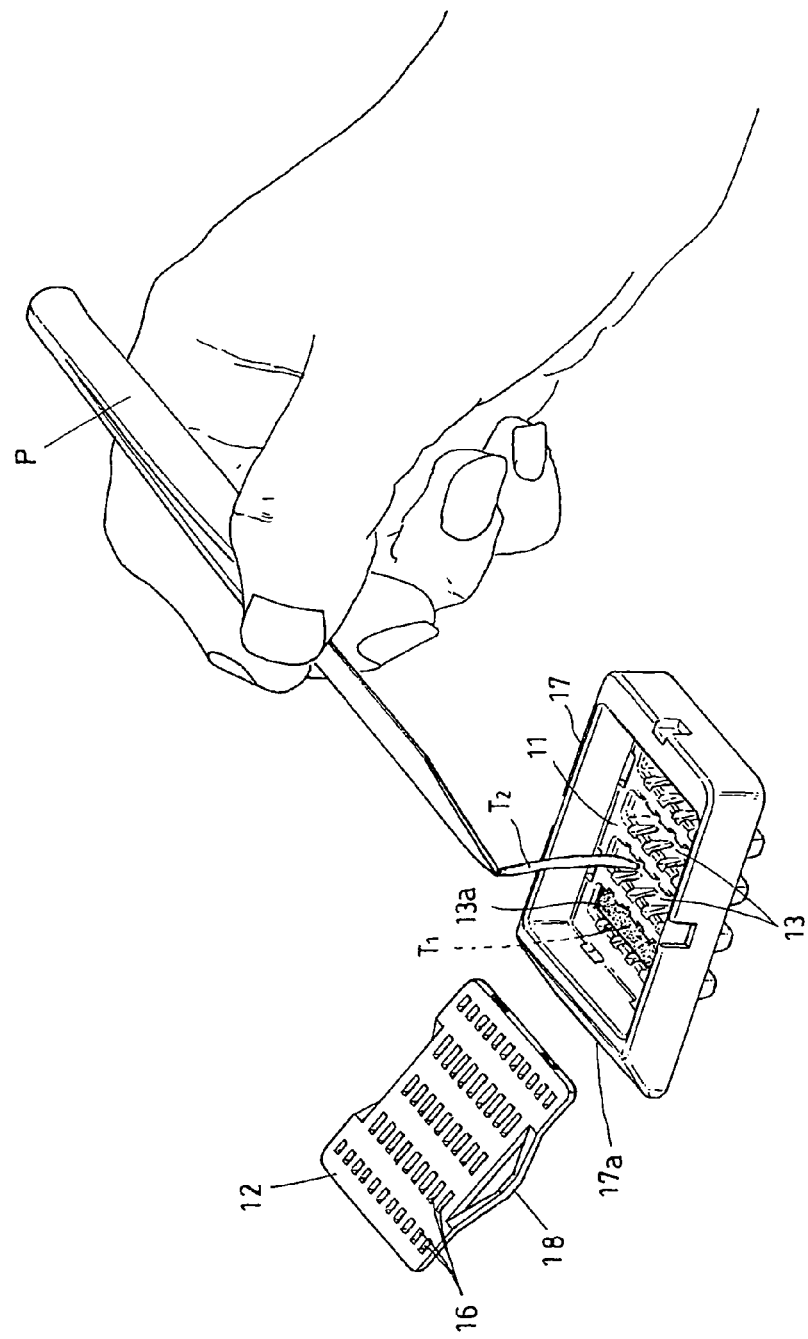
FIG. 12 shows how biopsy tissues are received in this cassette.

FIG. 12 schematically shows how biological tissues T2 are placed in the grooves 13 of the cassette 10B of the second embodiment using tweezers. In this case, the lid plate 12 and the sponge members 13a are removed from the base plate 11 beforehand. In this state, as shown in FIG. 12, biological tissues T1, T2, etc. are placed in the grooves 13 one after another, the sponge members 13a are placed on the biological tissues, and the lid plate 12 is placed on the base plate 11 to close the grooves. The cassette is then moved to a tissue laboratory. To close the lid plate 12, the protrusions 12a of the lid plate 12 are engaged in the respective engaging holes 16b of the base plate 11.

Because the sponge members 13a, which have elasticity sufficient to press and retain biological tissues, thereby preventing movement of the biological tissues and also pressing the biological tissues against the bottoms of the grooves, but not to crush the biological tissues, and which can be sliced, are separately prepared as the pressing/retaining members 13A, the pressing/retaining members can prevent the biological tissues inserted in the grooves 13 (tissue receiving portions) of the base plate 11 from moving when the lid plate 12 is closed.

FIG. 13 shows a sectional view corresponding to FIG. 5 of the first embodiment. After tissues have been inserted in the cassette, unlike the prior art shown in FIG. 9(b), the cassette is carried to a tissue laboratory without taking the biological tissues out of the cassette. In the tissue laboratory, the cassette is set in the automatic embedding device as it is, subjected to dehydration, and paraffin infiltration, and then embedded in paraffin, without taking the biological tissue specimens out of the cassette. As shown in FIG. 13(a), with the cassette received in the embedding dish 40, paraffin is poured into the dish 40. Then, as shown in FIG. 13(b), the cassette is taken out of the embedding dish 40, with the upper block Bp1 located upward. In this state, the cassette is mounted on the microtome as shown in FIG. 6(b), and the cassette is sliced.

In this embodiment, the embedding frame 41 is not used when pouring paraffin. Thus, this embodiment differs from the first embodiment in that the block Bp has no embedding frame 41 surrounding the lower block Bp2 of the first embodiment. Then the staining step is carried out in the same manner as in the first embodiment. In these steps, as shown in FIG. 9(a) and in the same manner as in the first embodiment, after biological tissues are placed in the cassette (arrow F1), the tissues are never taken out of the cassette until the slices of tissues are moved to the staining step (arrow F2).

Figure 14:
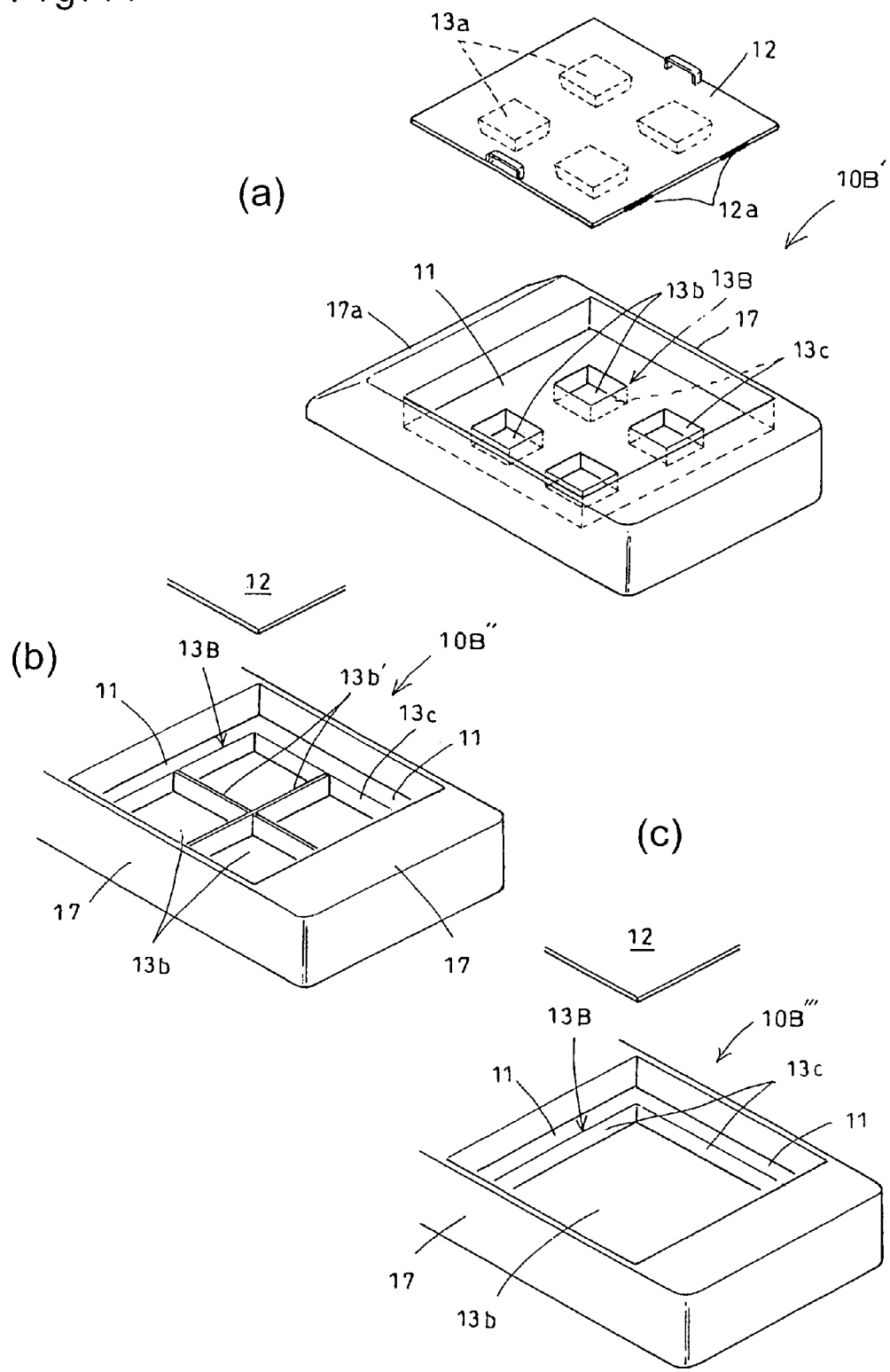
FIGS. 14(a) to 14(c) are exploded perspective views of cassettes for retaining biological tissues according to first to third modified examples of the second embodiment.

FIG. 14 shows three modified examples (cassettes 10B', 10B" and 10B''') of the second embodiment. In these examples too, the base plate 12 is detachable. Unless otherwise specifically stated, elements identical to those of the second embodiment are denoted by identical numerals. The cassette 10B' of the first modified example shown in FIG. 14(a) includes an edge plate 17 surrounding a base plate 11 formed with recesses 13b as tissue receiving portions and having frames 13c that protrude downwardly (i.e. protrude away from the lid plate 12) and defining the recesses 13b having a predetermined depth. While details of the holes 16, 16a and engaging holes 16b are not shown in FIGS. 14(a) to 14(c), they are identical in any of the modified examples to those of the second embodiment.

The cassette 10B" of the second modified example shown in FIG. 14(b) is a cassette for fixing, embedding and slicing a plurality of middle-sized biological tissues. In this example, too, like the grooves 13, the frame 13c and the partition plates 13b' defining the recesses 13b and the bottoms of the recesses 13b are made of a sliceable material thinner than the base plate 11. The cassette 10B''' of the third modified example shown in FIG. 14(c) is a cassette having a recess 13b (tissue receiving portion) of a predetermined depth defined by a downwardly protruding frame 13c and having a flat bottom. Like the grooves 13, the frame 13c defining the recess 13b and the bottom of the recess 13b are made of a sliceable material thinner than the base plate 11. This cassette is used to fix, embed and slice large-sized flat biological tissues.

FIG. 15 shows the test results of the adaptability (chemical resistance, heat resistance and sliceability) of materials for the plate members (sheets in the figure) and the sponge members. As is apparent from this table, the plate members can be advantageously made of any of polypropylene, vinyl, nylon and Teflon (registered trademark). The sponge members are most advantageously made of polyurethane in view of the above-mentioned resistances.

Figures 16, 17:
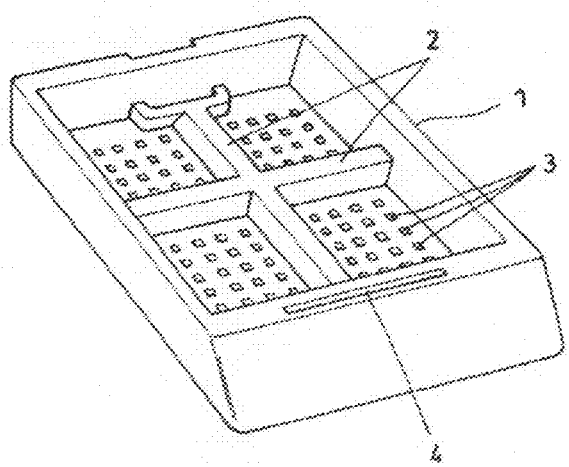
FIG. 16 is a view showing the results of a slicing/staining test conducted on cassettes for fixing, embedding and slicing biological tissues.
FIG. 17 is an external perspective view of a conventional container for placing biological tissues taken.

FIG. 16 shows the results of a slicing/staining test conducted on cassette for fixing, embedding and slicing biological tissues according to the second embodiment. Specifically, FIG. 16 shows photos of biopsy tissues embedded in paraffin, sliced tissues, and stained tissues, retained in the cassette according to the second embodiment and a conventional cassette (photos of the stained tissues are microscopic photos (HE staining ×200). With this method, it was possible to normally process tissues in the same manner as conventional methods.

INDUSTRIAL APPLICABILITY

The cassette for fixing, embedding and slicing biological tissues according to this invention includes a base plate on which biological tissues are placed, and a lid plate. Biological tissues are placed in tissue receiving portions of the cassette, and immovably pressed and retained by the pressing/retaining members, while introducing the fixing agent through the numerous small holes. The biological tissues are then cut to slices having a thickness of several micrometers with a microtome. The cassette can therefore be advantageously used in the field of morphological examination of tissues including clinical examination.

What is claimed is:

1. A cassette for fixing, embedding and slicing biological tissues, said cassette comprising:
    a base plate formed of a blank plate which has hardness and strength both higher than predetermined levels and on which biological tissues can be placed, the blank plate being formed of a material sliceable by a microtome; and
    a lid plate which is formed by bending the blank plate forming the base plate, or is formed of a separate blank plate and detachably coupled to the base plate,
    wherein the base plate has a tissue receiving portion for receiving biological tissues and for pressing and retaining the biological tissues between the tissue receiving portion and the lid plate, the tissue receiving portion being arranged to receive a pressing/retaining member for immovably pressing and retaining the biological tissues while being detachably coupled to the lid plate or provided separately from the lid plate, the base plate and the lid plate being formed with numerous small holes.

2. The cassette of claim 1, wherein the tissue receiving portion comprises grooves corresponding to strips of biological tissues, recesses corresponding to irregularly shaped biological tissues, or a recess having a flat bottom sufficient to receive irregularly shaped biological tissues.

3. The cassette of claim 2, wherein the material of which the blank plate is made is resistant to water, fixing agents, organic solvents, and embedding agents, and is resistant to temperature changes in the range of −30° C. to 65° C., and wherein the material is one of synthetic high-molecular weight compounds, specially treated paper and biological materials.

4. The cassette of claim 2, wherein the base plate has an edge plate provided along an outer edge of the base plate, and a support member provided on one side of the edge plate.

5. A method of fixing, embedding and slicing the cassette of claim 2, comprising:
placing biological tissues in the cassette;
pouring, immediately thereafter, an embedding agent for forming frozen pieces into the cassette;
closing the lid plate;
freezing the cassette; and
slicing the cassette with a cryostat.

6. The cassette of claim 1, wherein the material of which the blank plate is made is resistant to water, fixing agents, organic solvents, and embedding agents, and is resistant to temperature changes in the range of −30° C. to 65° C., and wherein the material is one of synthetic high-molecular weight compounds, specially treated paper and biological materials.

7. The cassette of claim 6, wherein the base plate has an edge plate provided along an outer edge of the base plate, and a support member provided on one side of the edge plate.

8. A method of fixing, embedding and slicing the cassette of claim 6, comprising:
placing biological tissues in the cassette;
pouring, immediately thereafter, an embedding agent for forming frozen pieces into the cassette;
closing the lid plate;
freezing the cassette; and
slicing the cassette with a cryostat.

9. The cassette of claim 1, wherein the base plate has an edge plate provided along an outer edge of the base plate, and a support member provided on one side of the edge plate.

10. A method of fixing, embedding and slicing the cassette of claim 9, comprising:
placing biological tissues in the tissue receiving portion of the base plate;
closing the lid plate;
immersing the cassette in a fixing agent;
fixing the biological tissues with the pressing/retaining member;
setting the cassette in an automatic embedding device;
dehydrating the cassette;
placing the cassette in an embedding agent infiltration tank to infiltrate an embedding agent into the biological tissues in the cassette;
removing the cassette from the automatic embedding device;
placing the cassette in an embedding dish;
pouring an embedding agent into the embedding dish from over the cassette, thereby embedding the cassette in the embedding agent;
removing the cassette from the embedding dish to form a block containing the cassette;
setting the block on a microtome for forming tissue slices; and
slicing the block.

11. A method of fixing, embedding and slicing the cassette of claim 9, comprising:
placing biological tissues in the cassette;
pouring, immediately thereafter, an embedding agent for forming frozen pieces into the cassette;
closing the lid plate;
freezing the cassette; and
slicing the cassette with a cryostat.

12. A method of fixing, embedding and slicing the cassette of claim 1, comprising:
placing biological tissues in the cassette;
pouring, immediately thereafter, an embedding agent for forming frozen pieces into the cassette;
closing the lid plate;
freezing the cassette; and
slicing the cassette with a cryostat.

* * * * *